US012594051B2

(12) United States Patent
White

(10) Patent No.: US 12,594,051 B2
(45) Date of Patent: Apr. 7, 2026

(54) ULTRASOUND MICROVASCULATURE SUPER-RESOLUTION IMAGING ACQUISITION

(71) Applicant: FUJIFILM SonoSite, Inc., Bothell, WA (US)

(72) Inventor: Christopher White, North Vancouver (CA)

(73) Assignee: FUJIFILM SonoSite, Inc., Bothell, WA (US)

( * ) Notice: Subject to any disclaimer, the term of this patent is extended or adjusted under 35 U.S.C. 154(b) by 212 days.

(21) Appl. No.: 18/346,630

(22) Filed: Jul. 3, 2023

(65) Prior Publication Data

US 2025/0009327 A1    Jan. 9, 2025

(51) Int. Cl.
A61B 8/06        (2006.01)
A61B 8/00        (2006.01)

(52) U.S. Cl.
CPC ............... A61B 8/06 (2013.01); A61B 8/488 (2013.01); A61B 8/5207 (2013.01); A61B 8/5223 (2013.01); A61B 8/5269 (2013.01); A61B 8/5284 (2013.01)

(58) Field of Classification Search
None
See application file for complete search history.

(56) References Cited

U.S. PATENT DOCUMENTS

2008/0285819 A1 * 11/2008 Konofagou ............ A61B 8/485
                                                           382/128
2013/0090560 A1 * 4/2013 Kotaki .................... A61B 8/54
                                                           600/443

OTHER PUBLICATIONS

Bourquin et al., "In Vivo Pulsatility Measurement of Cerebral Microcirculation in Rodents Using Dynamic Ultrasound Localization Microscopy," (Oct. 28, 2021), IEEE Transactions on Medical Imaging ( vol. 41, Issue: 4, Apr. 2022). (Year: 2022).*
Burgess et al., "Slow-Flow Ultrasound Localization Microscopy Using Recondensation of Perfluoropentane Nanodroplets," (May 2022), Ultrasound in Medicine & Biology, vol. 48, Issue 5, May 2022, pp. 743-759. (Year: 2022).*

* cited by examiner

*Primary Examiner* — Keith M Raymond
*Assistant Examiner* — Ashish S. Jasani
(74) *Attorney, Agent, or Firm* — Colby Nipper PLLC

(57) ABSTRACT

Systems and methods for microvasculature imaging acquisition are disclosed. In aspects, a full frame corresponding to a field of view of an ultrasound scanner is divided into small portions, each of which is individually scanned for a desired period of time at a higher frame rate than the ultrasound scanner is capable of using to scan the full frame. These ultrasound data acquisition techniques enable super-resolution image processing or high-sensitivity microvascular-doppler image processing to be used to track low-intensity, slow-flow microvasculature of an anatomy of a subject.

21 Claims, 11 Drawing Sheets

400

100

200

300

400

500

600

<u>700</u>

800

900

Figure 10:
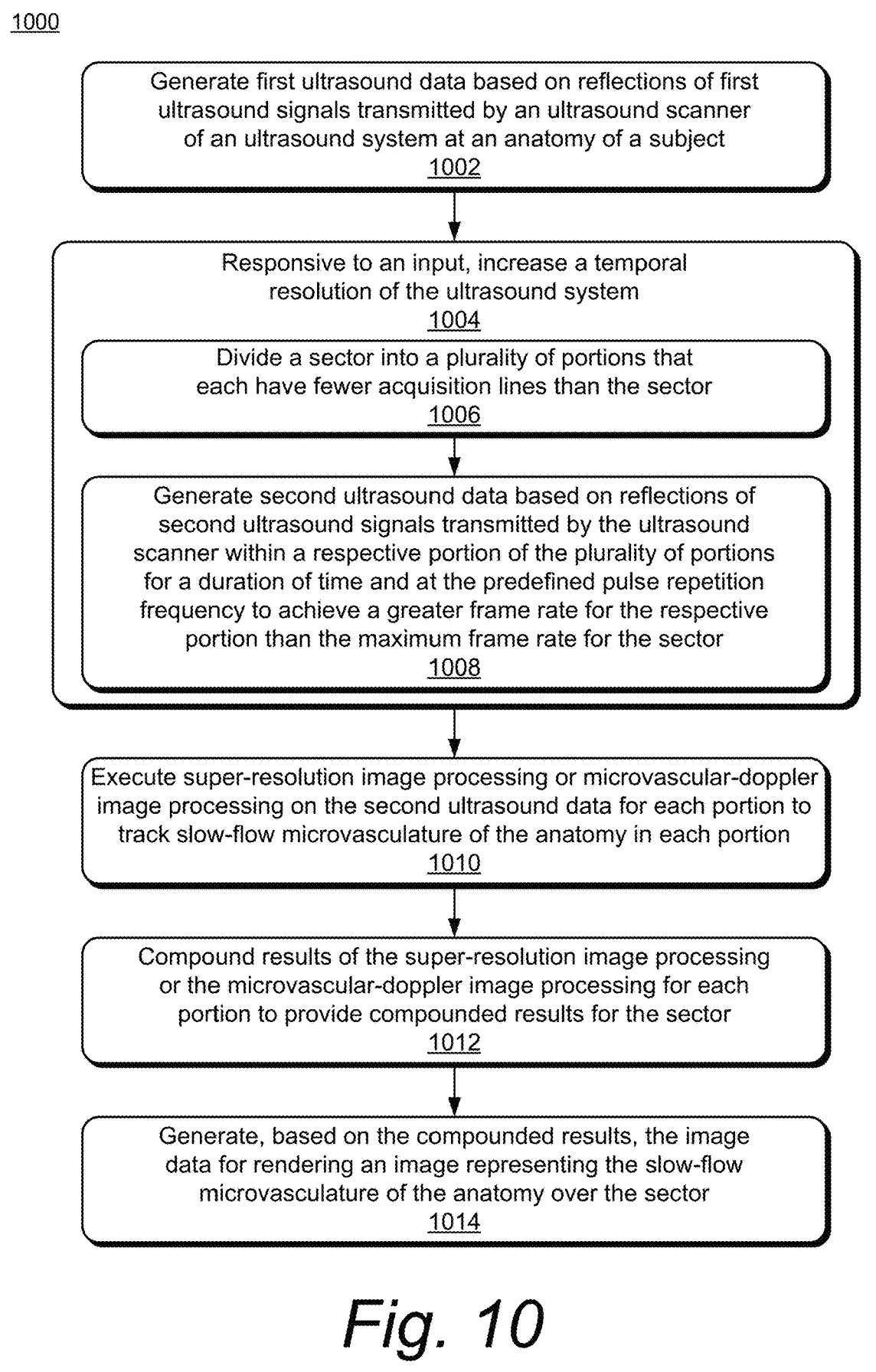

1000

Generate first ultrasound data based on reflections of first
ultrasound signals transmitted by an ultrasound scanner
of an ultrasound system at an anatomy of a subject
1002

Responsive to an input, increase a temporal
resolution of the ultrasound system
1004

Divide a sector into a plurality of portions that
each have fewer acquisition lines than the sector
1006

Generate second ultrasound data based on reflections of
second ultrasound signals transmitted by the ultrasound
scanner within a respective portion of the plurality of portions
for a duration of time and at the predefined pulse repetition
frequency to achieve a greater frame rate for the respective
portion than the maximum frame rate for the sector
1008

Execute super-resolution image processing or microvascular-doppler
image processing on the second ultrasound data for each portion to
track slow-flow microvasculature of the anatomy in each portion
1010

Compound results of the super-resolution image processing
or the microvascular-doppler image processing for each
portion to provide compounded results for the sector
1012

Generate, based on the compounded results, the image
data for rendering an image representing the slow-flow
microvasculature of the anatomy over the sector
1014

ULTRASOUND MICROVASCULATURE SUPER-RESOLUTION IMAGING ACQUISITION

BACKGROUND

Conventional ultrasound techniques for acquiring high-resolution, high-sensitivity images for low-intensity, slow-flow microvasculature of anatomy, such as tumors, a liver, a kidney, etc., have many limitations, including long acquisition times and long processing times. Additional challenges arise due to these techniques being used with motion-sensitive equipment on a breathing, moving subject. One approach, for example, is super-resolution imaging (also referred to as micro-bubble tracking), which acquires image frames, localizes and tracks micro bubbles, and generates a super-resolution image of the vasculature (e.g., a zero-radius track of the bubble path). Another approach is high-sensitivity power-doppler imaging, which provides images displaying the strength of the doppler signal in color, rather than speed and direction information.

Generally, techniques used to acquire the ultrasound data for super-resolution and power-doppler imaging include plane-wave acquisition and B-mode acquisition. Plane-wave acquisition excites all available transducer elements with different angles to scan an entire frame width with a single transmit pulse. However, due to the high data bandwidth of plane-wave techniques, the acquisition length is often limited by the amount of direct onboard Field Programmable Gate Array (FPGA) ram, for example 8 gigabytes (GB), which is filled up after only a few seconds. This does not provide sufficient amount of data (e.g., one to two minutes of acquisition) for bubble tracking. Further, plane-wave acquisitions have low resolution due to a lack of transmit beamforming and no receive beamformer (per line). Plane-wave acquisitions also frequently require multiple angles to improve resolution, which significantly reduces their frame rate (e.g., down to about 1,000 frames per second (fps)). B-mode acquisition uses a linear array of transducers to simultaneously scan a plane through a subject that can be viewed as a two-dimensional (2D) image on a screen. However, B-mode data, partially because of the heavy processing used to produce a high-quality image, is not well suited to bubble tracking and can actually filter out some of the micro-bubble signals. B-mode data is usually processed as 8-bit log compressed, which does not provide a suitable dynamic range for optimal processing or provide directional information. Further, B-mode frame rates (e.g., 300-400 fps and often less) are too low and typical B-mode cine loop sizes (e.g., 300 frames) are too small for high-resolution imaging (e.g., 1,000+ fps, 10,000+ frames).

Accordingly, conventional techniques for acquiring high-resolution, high-sensitivity images are not well suited for low-intensity, slow-flow microvasculature of anatomy. The limitations in these conventional techniques can lead to a poor user experience and sub-optimal imaging results.

SUMMARY

Systems and methods for microvasculature imaging acquisition are disclosed. In aspects, a full frame corresponding to a field of view of an ultrasound scanner is divided into small portions, each of which is individually scanned for a desired period of time at a higher frame rate than the ultrasound scanner is capable of using to scan the full frame. These ultrasound data acquisition techniques enable super-resolution image processing or high-sensitivity power-doppler image processing to be used to track low-intensity, slow-flow microvasculature of an anatomy of a subject.

In some aspects, a method for microvasculature imaging acquisition is disclosed. The method includes generating first ultrasound data based on reflections of first ultrasound signals transmitted by an ultrasound scanner of an ultrasound system at an anatomy of a subject. In aspects, the ultrasound scanner has (i) a predefined pulse repetition frequency for emitting the first ultrasound signals and (ii) a maximum frame rate for producing multiple frames of image data from the first ultrasound data over a sector corresponding to a full field of view of the ultrasound scanner. The sector has a width corresponding to an image width of the multiple frames. Also, the maximum frame rate is based on the predefined pulse repetition frequency and a number of acquisition lines corresponding to each frame of the image data. The method also includes, responsive to an input, increasing a temporal resolution of the ultrasound system by (i) dividing the sector into a plurality of portions that each have fewer acquisition lines than the sector and (ii) generating second ultrasound data based on reflections of second ultrasound signals transmitted by the ultrasound scanner within a respective portion of the plurality of portions for a duration of time and at the predefined pulse repetition frequency to achieve a greater frame rate for the respective portion than the maximum frame rate for the sector. In addition, the method includes executing super-resolution image processing or microvascular-doppler image processing on the second ultrasound data for each portion to track slow-flow microvasculature of the anatomy in each portion. Further, the method includes compounding results of the super-resolution image processing or the microvascular-doppler image processing for each portion to provide compounded results for the sector. Also, the method includes generating, based on the compounded results, the image data for rendering an image representing the slow-flow microvasculature of the anatomy over the sector.

In some aspects, an ultrasound system is disclosed. The ultrasound system includes an ultrasound scanner, one or more computer processors, and one or more computer-readable media. The ultrasound scanner has a predefined pulse repetition frequency for emitting ultrasound signals and a maximum frame rate for producing multiple frames of image data from detected reflections of the first ultrasound signals emitted over a sector corresponding to a full field of view of the ultrasound scanner. The sector has a width corresponding to an image width of the multiple frames. The maximum frame rate is based on the predefined pulse repetition frequency and a number of acquisition lines corresponding to each frame of the image data. The ultrasound scanner is also configured to, in response to an input, divide the sector into a plurality of portions and transmit, at an anatomy of a subject, the ultrasound signals within a respective portion of the plurality of portions repeatedly for a predefined duration of time using the predefined pulse repetition frequency to achieve a frame rate for the respective portion that is greater than the maximum frame rate for the sector. Further, the ultrasound scanner is configured to generate ultrasound data for the respective portion of the plurality of portions based on detected reflections of the ultrasound signals transmitted within the respective portion. The computer-readable media has instructions stored thereon that, responsive to execution by the one or more computer processors, implement one or more modules, the one or more modules configured to (i) execute super-resolution image processing or microvascular-doppler image processing on the ultrasound data for each portion to provide image-processing results for tracking slow-flow microvasculature of the anatomy and (ii) generate the image data for rendering an image representing the slow-flow microvasculature of the anatomy over the sector based on a combination of the image-processing results of the ultrasound data for each portion.

In some aspects, a method of microvasculature imaging acquisition is disclosed. The method includes acquiring, by an ultrasound system having an ultrasound scanner with a fixed pulse repetition frequency for emitting ultrasound signals, a first subset of a full set of data acquisition lines corresponding to a frame of image data, the first subset acquired repeatedly over a first time period using a first frame rate and the fixed pulse repetition frequency to generate first ultrasound data, the ultrasound data representing reflections of the ultrasound signals transmitted by the ultrasound scanner at an anatomy of a subject, the first subset having fewer data acquisition lines than the full set. The method also includes acquiring, by the ultrasound system and independent of the first subset of the data acquisition lines, a second subset of the full set of data acquisition lines corresponding to the frame of image data, the second subset acquired repeatedly over a second time period using a second frame rate and the fixed pulse repetition frequency to generate second ultrasound data, the second subset having fewer data acquisition lines than the full set. The method further includes tracking slow-flow microvasculature of the anatomy by executing super-resolution-image processing or microvascular-doppler image processing on the first ultrasound data and the second ultrasound data. Also, the method includes generating image data representing the slow-flow microvasculature of the anatomy based on a combination of image-processing results for the first ultrasound data and the processed second ultrasound data.

BRIEF DESCRIPTION OF THE DRAWINGS

The appended drawings illustrate examples and are, therefore, exemplary embodiments and not considered to be limiting in scope.

FIG. 10 depicts a method for microvasculature imaging acquisition.

DETAILED DESCRIPTION

Figure 1:
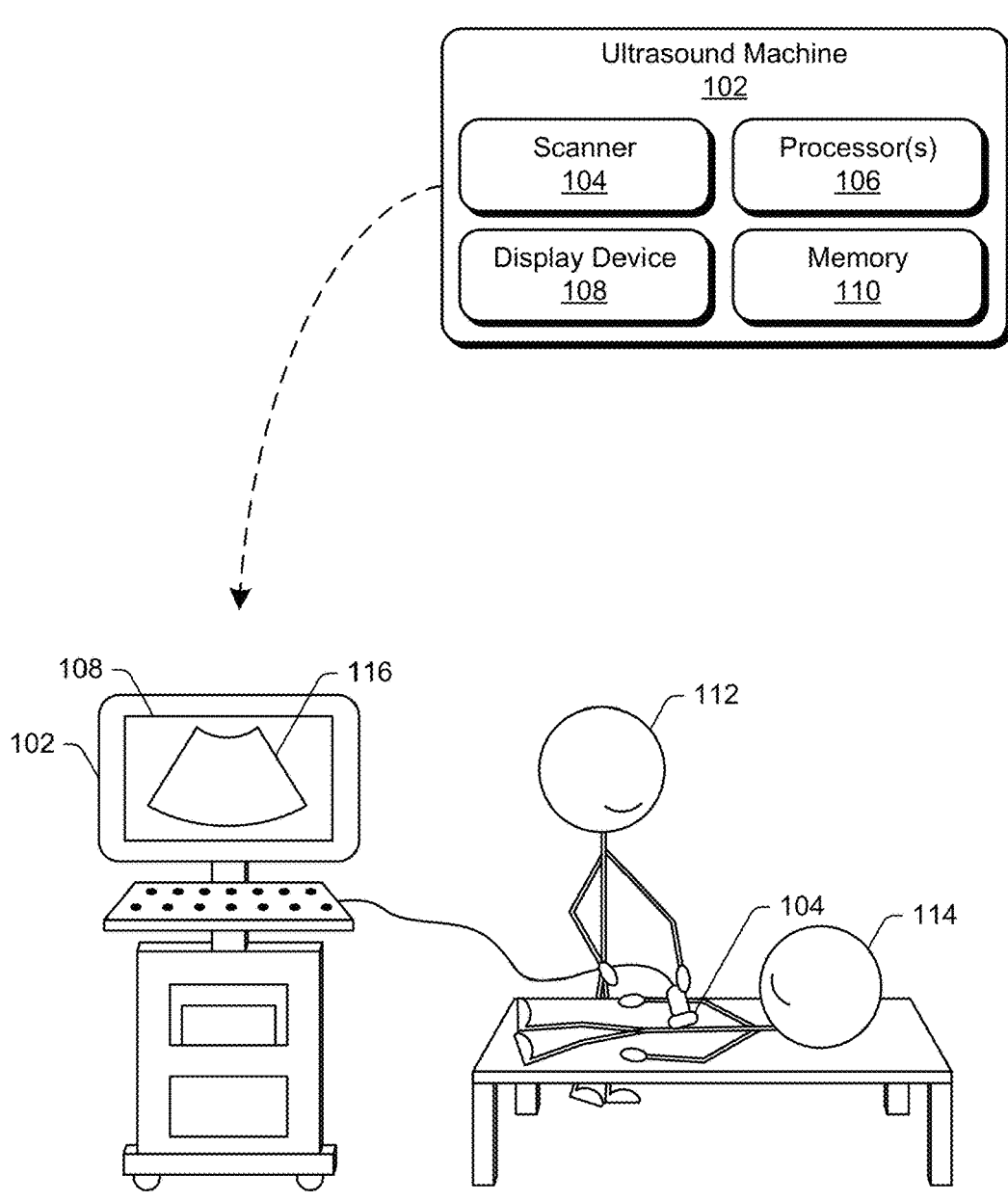
FIG. 1 illustrates an example environment for an ultrasound system having an ultrasound scanner, in accordance with one or more implementations.

Conventional techniques for acquiring high-resolution, high-sensitivity images have significant limitations for low-intensity, slow-flow microvasculature of anatomy. Super-resolution imaging and microvascular-doppler imaging are two example processes that can provide high-resolution images; however, these imaging processes are limited by the conventional techniques for the acquisition of ultrasound data.

Super-resolution imaging can produce highly detailed images resulting in a large degree of available quantitative metrics, but such imaging is extremely technical. For example, super-resolution imaging requires full frame imaging at frame rates exceeding 1,000 frames per second (fps) (e.g., 2000 fps, 3000 fps) and has traditionally been applied to plane-wave imaging acquisitions because of its potential for high-frame rate acquisition. Such high frame rates are required to track moving microbubbles in the anatomy; if the frame rate is too low, it is not possible to isolate the movement of individual bubbles accurately. Super-resolution imaging requires a significant amount of data (e.g., on the order of minutes) and a significantly high level of processing with many user-selected parameters and many chances for incorrect selection. Due to long scan times and a high sensitivity to motion, super-resolution imaging does not apply well to three-dimensional (3D) acquisitions or to any applications where the anatomy is not motionless over the duration of the acquisition. Resolving some of these limitations can enable super-resolution imaging to be a highly effective tool to produce high-quality images of slow-flow microvasculature of anatomy.

Conventional data acquisition techniques (e.g., B-mode, plane-wave) have technical limitations that prevent super-resolution from being usable for imaging slow-flow microvasculature of anatomy. For example, B-mode images are optimized for visualization of general anatomy (often log compressed, 8-bit processed) and thus is not well suited to bubble tracking at least because it can filter out low intensity microbubbles. Also, B-mode data is 8-bit compressed, which does not provide a suitable dynamic range for optimal processing and does not provide directional information. Further, B-mode frame rates are too low (300-400 fps maximum) for the required 1,000+ fps of super-resolution imaging, and B-mode cine-loop sizes (typically 100-300 frames) are too small for super-resolution imaging, which needs cine-loop sizes over 10,000+ frames. Due to the high data bandwidth of plane-wave techniques, the acquisition length is often limited by the amount of direct onboard FPGA ram, for example 8 gigabytes (GB), which is filled up after only a few seconds. This does not, however, provide sufficient amount of data (e.g., one to two minutes of acquisition) for bubble tracking. Plane-wave acquisitions also have poor resolution due to a lack of per-line transmit beamforming and no per-line receive beamformer. Further, plane-wave acquisitions frequently require acquisitions using multiple angles to improve resolution, which significantly lowers the frame rate (down to about 1,000 fps or less depending on the number of compounding angles acquired).

A high-sensitivity power-doppler imaging technique (e.g., color velocity doppler, power directional doppler, etc.) is an alternative approach to acquire high-quality ultrasound images for blood flow in vessels. Generally, power-doppler acquisition uses an ensemble of 8, 16, 32, etc. pulses to generate a power-doppler signal (via filtering out a stationary, non-moving signal). However, slow flow and weak doppler signals are generally lost in the noise with such short ensemble sizes. Accordingly, much higher ensemble sizes and much more sensitive processing, while maintaining a reasonable total acquisition time, are required for imaging slow flow vasculature. Resolving some of the limitations of the power doppler can provide a data acquisition technique that (i) has an acquisition time many times faster than that of super-resolution imaging, (ii) is applicable to 3D acquisitions, (iii) has fewer processing parameters and more deterministic and predictable processing results, and (iv) is comparatively as sensitive as super-resolution imaging.

Super-resolution imaging, when it works, provides many metrics that can be determined from bubble tracks (e.g., velocity, tortuosity, branching, etc.). In comparison to super-resolution, power doppler has fewer measurable features but likely generally includes a majority of the information an operator is looking for in a package that is simple, predictable, and achievable (and 3D).

The techniques disclosed herein for microvasculature imaging acquisition solve many of the above-described limitations to enable super-resolution imaging and power-doppler imaging of slow-flow microvasculature of anatomy. For example, microvasculature imaging acquisition enables an ultrasound system to acquire ultrasound data at a higher frame rate than the ultrasound system is capable of using for a full image. This faster frame rate is achievable by instead acquiring portions (e.g., sections, chunks, blocks, quadrants, etc.) of the image frame. The acquisition workflow handles acquisition of the complete frame by acquiring sequentially these small portions of the image. Such acquisition provides a repeated, consistent sequence of data for each portion at a desired frame rate. Then, the data can be combined to generate the complete image (full frame). Further details are disclosed below.

As described herein, a frame is the accumulation of data acquisition lines usable to generate an ultrasound image. A line is a vertical collection of samples (in the depth direction) positioned horizontally across the face of the transducer. For example, a transducer might have a field-of-view (FOV) of 10 mm using an array consisting of 256 piezoelectric elements which could result in, for example, 256 or 512 separate lines spaced across the 10 mm width. A full field-of-view image, in this example, would thus consist of acquisition of 256 (or 512) lines. As one skilled in the art can appreciate, this description can be extended for different transducer types, such as linear, curved, or phased array. A frame rate is the number of frames per second (fps) and is generally measured in hertz (Hz). Data acquisition lines are acquired based on a pulses emitted by a transducer (e.g., scanner) of an ultrasound machine. Pulse repetition frequency (PRF) is the number of pulses emitted per second by the transducer. The pulses are spaced to provide sufficient time between pulses for the transmit beam to reach the target and reflect back to the transducer before the next pulse is generated. Generally, PRF is measured in kilohertz (kHz).

Example Ultrasound System

FIG. 1 illustrates an example environment for an ultrasound system 100 having an ultrasound scanner, in accordance with one or more implementations. Generally, the ultrasound system 100 includes an ultrasound machine 102, which generates data based on high-frequency sound waves reflecting off body structures. The ultrasound machine 102 includes various components, some of which include a scanner 104, one or more processors 106, a display device 108, and a memory 110.

A user 112 (e.g., nurse, ultrasound technician, operator, sonographer, etc.) directs the scanner 104 toward a patient 114 to non-invasively scan internal bodily structures (e.g., organs, tissues, etc.) of the patient 114 for testing, diagnostic, or therapeutic reasons. In some implementations, the scanner 104 includes an ultrasound transducer array and electronics communicatively coupled to the ultrasound transducer array to transmit ultrasound signals to the patient's anatomy and receive ultrasound signals reflected from the patient's anatomy. In some implementations, the scanner 104 is an ultrasound scanner, which can also be referred to as an ultrasound probe.

The display device 108 is coupled to the processor 106, which processes the reflected ultrasound signals to generate ultrasound data. The display device 108 is configured to generate and display an ultrasound image (e.g., ultrasound image 116) of the anatomy based on the ultrasound data generated by the processor 106 from the reflected ultrasound signals detected by the scanner 104. In some aspects, the ultrasound data includes the ultrasound image 116 or data representing the ultrasound image 116.

Figure 2:
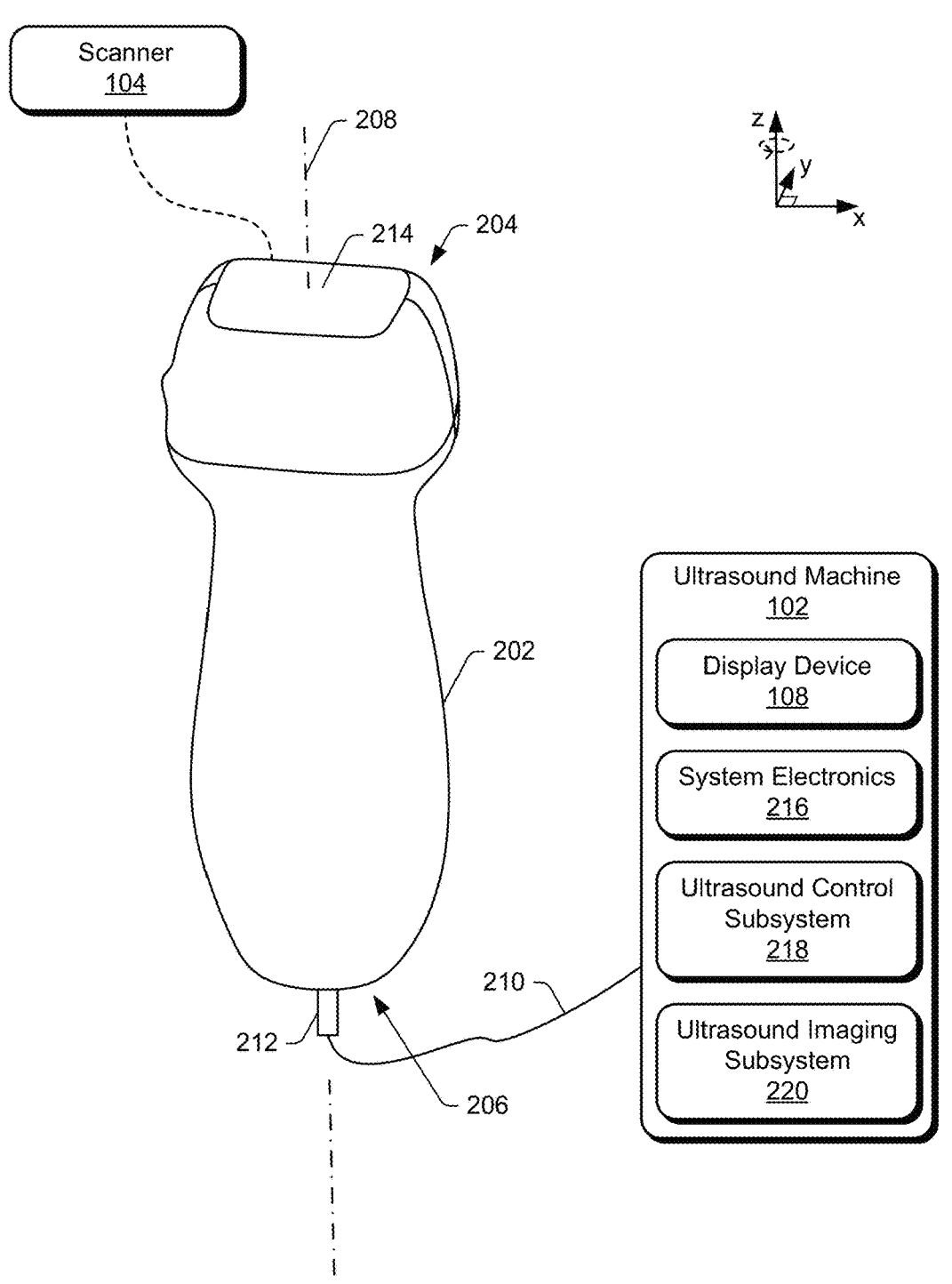
FIG. 2 illustrates an example implementation of the ultrasound scanner from FIG. 1.

FIG. 2 illustrates an example implementation 200 of the ultrasound scanner 104 from FIG. 1. The scanner 104 (e.g., ultrasound scanner) includes an enclosure 202 extending between a distal end portion 204 and a proximal end portion 206. The enclosure 202 includes a central axis 208 (e.g., longitudinal axis) that intersects the distal end portion 204 and the proximal end portion 206. The central axis 208 corresponds to an axial direction of the scanner 104. The scanner 104 is electrically coupled to an ultrasound imaging system (e.g., the ultrasound machine 102) via a cable 210 that is attached to the proximal end portion 206 of the scanner 104 by a strain-relief element 212. In some implementations, the scanner 104 is wirelessly coupled to the ultrasound imaging system and communicates with the ultrasound imaging system via one or more wireless transmitters, receivers, or transceivers over a wireless connection or network (e.g., Bluetooth™, Wi-Fi™, etc.).

A transducer assembly 214 having one or more transducer elements is electrically coupled to system electronics 216 in the ultrasound machine 102. In operation, the transducer assembly 214 transmits ultrasound energy from the one or more transducer elements toward a subject and receives ultrasound echoes from the subject. The ultrasound echoes are converted into electrical signals by the transducer element(s) and electrically transmitted to the system electronics 216 in the ultrasound machine 102 for processing and generation of one or more ultrasound images.

Capturing ultrasound data from a subject using a transducer assembly (e.g., the transducer assembly 214) generally includes generating ultrasound signals, transmitting ultrasound signals into the subject, and receiving ultrasound signals reflected by the subject. A wide range of frequencies of ultrasound can be used to capture ultrasound data, such as, for example, low-frequency ultrasound (e.g., less than 15 Megahertz (MHz)) and/or high-frequency ultrasound (e.g., greater than or equal to 15 MHZ). A particular frequency range to use can readily be determined based on various factors, including, for example, depth of imaging, desired resolution, and so forth.

In some implementations, the system electronics 216 include one or more processors (e.g., the processor(s) 106 from FIG. 1), integrated circuits, application-specific integrated circuits (ASICs), FPGAs, and power sources to support functioning of the ultrasound machine 102. In some implementations, the ultrasound machine 102 also includes an ultrasound control subsystem 218 having one or more processors. At least one processor, FPGA, or ASIC causes electrical signals to be transmitted to the transducer(s) of the scanner 104 to emit sound waves and also receives electrical pulses from the scanner 104 that were created from the returning echoes. One or more processors, FPGAs, or ASICs process the raw data associated with the received electrical pulses and form an image that is sent to an ultrasound imaging subsystem 220, which causes the image (e.g., the image 116 in FIG. 1) to be displayed via the display device 108. Thus, the display device 108 displays ultrasound images from the ultrasound data processed by the processor(s) of the ultrasound control subsystem 218.

In some implementations, the ultrasound machine 102 also includes one or more user input devices (e.g., a keyboard, a cursor control device, a microphone, a camera, etc.) that input data and enable taking measurements from the display device 108 of the ultrasound machine 102. The ultrasound machine 102 can also include a disk storage device (e.g., computer-readable storage medium such as read-only memory (ROM), a Flash memory, a dynamic random-access memory (DRAM), a NOR memory, a static random-access memory (SRAM), a NAND memory, and so on) for storing the acquired ultrasound images. In addition, the ultrasound machine 102 can include a printer that prints the image from the displayed data. To avoid obscuring the techniques described herein, such user input devices, disk storage device, and printer are not shown in FIG. 2.

Figure 3:
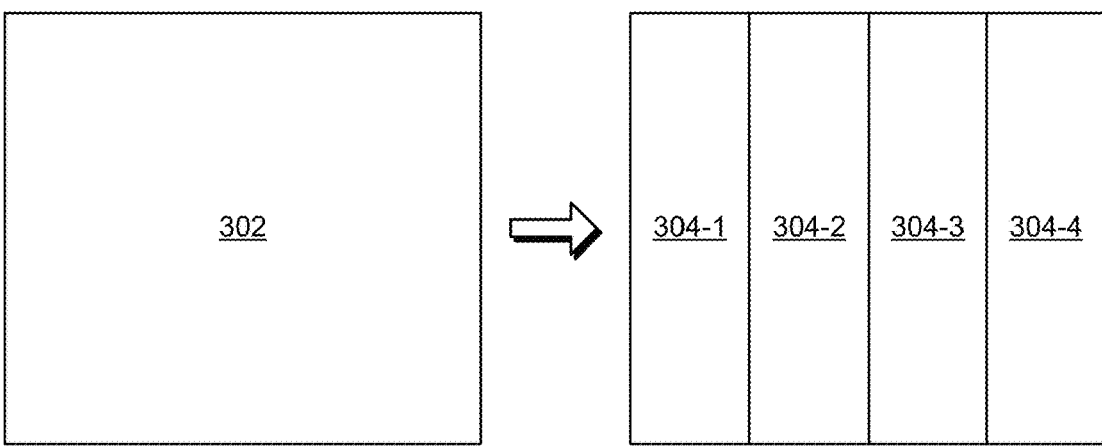
FIG. 3 illustrates an example of ultrasound data acquisition in accordance with implementations disclosed herein.

FIG. 3 illustrates an example 300 of ultrasound data acquisition in accordance with implementations disclosed herein. Generally, a full frame (e.g., frame 302) is acquired at a particular frame rate (e.g., 500 fps) using conventional acquisition techniques (e.g., B-mode). However, using the acquisition techniques disclosed herein, small portions of the frame 302 can be acquired at significantly greater frame rates. For example, acquisition of one-quarter of the width of an image can be performed four times faster than acquisition of the full image. The portions can be any suitable size smaller than the full frame, to a limit of one acquisition line.

In the illustrated example, a full frame (e.g., the frame 302) is divided into four portions (e.g., portions 304-1, 304-2, 304-3, and 304-4). The full frame 302 contains 256 image lines (and a variable number of samples, e.g., 512 samples) and is acquired at a rate of 250 fps (also referred to as hertz (Hz)). Because frame rate is based on the pulse repetition frequency (PRF) divided by the number of acquisition lines, the frame rate can be increased when using a fixed PRF by decreasing the number of acquisition lines. For example, when divided into the four portions 304, each of 64 image lines, each portion 304 can be acquired at 1,000 fps instead of the 250 fps used for the full frame 302. If the frame 302 is divided into eight portions, each portion can be acquired at 2000 fps. Accordingly, a frame can be divided into any suitable number of portions (to the minimum size limit of one image line) to significantly increase the acquisition frame rate of each portion (e.g., by a factor of the total number of non-overlapping portions). In some implementations, the frame is divided into at least two non-overlapping portions. In some other implementations, the frame is divided into at least two overlapping portions. The described acquisition mode can provide a repeated, consistent sequence of data for each portion 304 at a desired frame rate. Each portion 304 is acquired for a desired acquisition time (referred to as "line-time") (e.g., 1 second, 2 seconds, 5 seconds, 10 seconds, etc.).

Figure 4:
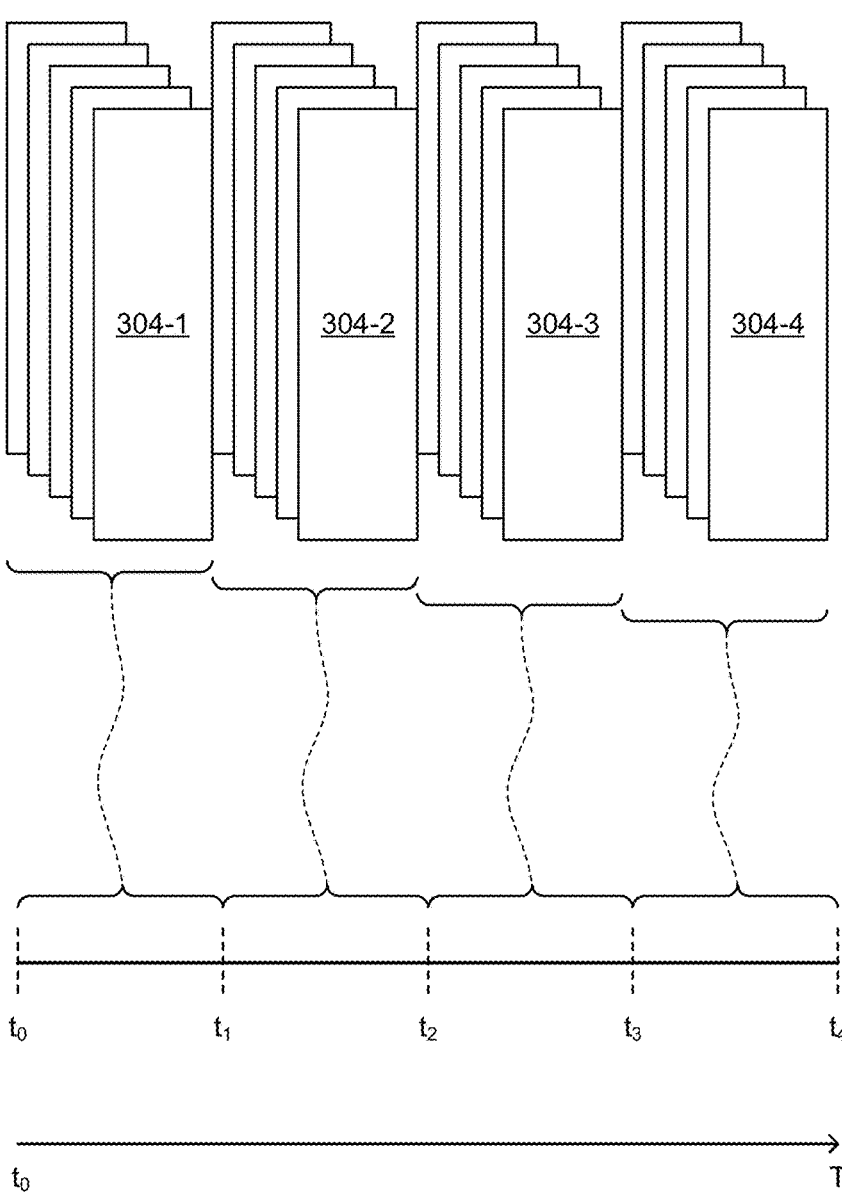
FIG. 4 illustrates an example of a plurality of data blocks arranged in groups.

Consider FIG. 4, which illustrates an example 400 of a plurality of data blocks arranged in groups. After data is acquired for one portion 304 over the line-time, acquisition of a next portion 304 begins. For example, a first portion (e.g., portion 304-1) is acquired repeatedly over a duration of time (e.g., 1 second) from time to $t_0$ time $t_1$. After acquisition of the first portion is complete (at time $t_1$), acquisition of a second portion (e.g., portion 304-2) adjacent to the first portion begins and continues repeatedly until time $t_2$. Then, acquisition of a third portion (e.g., portion 304-3) adjacent to the second portion begins and continues repeatedly until time $t_3$. Finally, at time $t_3$, acquisition of a fourth portion (e.g., portion 304-4) adjacent to the third portion begins and continues repeatedly until time $t_4$. In some instances, a time delay can exist between acquisitions of adjacent portions. In some implementations, the portions 304 can be acquired in any order.

The total acquisition time (e.g., time T) for the data acquisition is line-time (e.g., $t_n$-$t_{n-1}$ assuming no time delay between portions) multiplied by the number of portions 304. In the illustrated example, the total acquisition time T is determined by multiplying line-time (e.g., $t_1$-$t_0$) by four (e.g., four portions). Thus, increasing the required fps increases the acquisition time (to a maximum fps corresponding to a portion size of only one image line, resulting in the final acquisition time is total-image-lines (e.g., 256 in the illustrated example) multiplied by line-time). In a single-line acquisition example, using a portion size of one image line provides not only a maximum fps but also a maximum acquisition time for the full image. However, using multiline acquisition, which acquires multiple lines simultaneously, can reduce the total acquisition time (e.g., by half for a 2× multiline). Multiline acquisition is a process by which multiple lines are generated using a single transmit pulse.

Continuing the example, the data of each acquired portion 304 can be treated as a collection of images (e.g., images that are 64×512 pixels), where each image is acquired at 1/1000 seconds(s) intervals (1,000 Hz). The data of each acquired portion 304 can also be treated on a per-line basis. For example, by extracting the nth line from each portion 304, a sequence of data for that single line can be constructed. Such processing is similar to M-mode (motion mode) ultrasound imaging, which is defined as a time-motion display of an ultrasound wave along a chosen ultrasound line and can be used to provide a unidimensional view of the heart, for example. Returning to the illustrated example, the PRF of the sequence of data for each portion 304 is also 1,000 Hz. In such a configuration, alternate processing can be performed on the sequence of data in each portion. In this example, the effective PRF is 1,000 Hz as would be achieved by breaking a full width image acquisition of 250 fps into 4 groups. It can also be understood that by breaking the image into 8 groups, the effective PRF would be 2,000 Hz.

Figure 5:
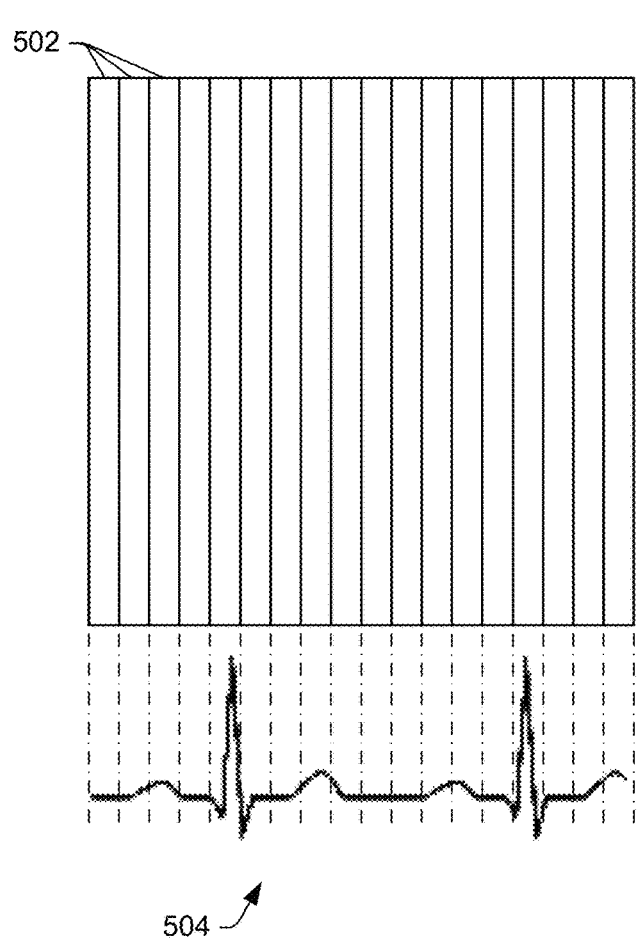
FIG. 5 illustrates an example of ultrasound data acquisition with individual acquisition lines synchronized with information from an echocardiograph (ECG) cycle.

FIG. 5 illustrates an example of ultrasound data acquisition 500 with individual acquisition lines 502 synchronized with information from an echocardiograph (ECG) cycle. Each line acquired can be associated with a timestamp. In single-line acquisition, no two lines are acquired at exactly the same time. However, multiline acquisition can acquire two or more lines at the same time and therefore those two or more lines can have the same timestamp. Within the time frame of the total acquisition for the image, each line can be associated with a region of the total acquisition, based on the line's corresponding timestamp. Accordingly, the timestamps can help arrange the acquisition lines in a correct sequential order (e.g., for generating a final complete image), particularly when acquiring repeatedly a small portion of the total acquisition (and while scanning moving elements). In an example, the ultrasound system synchronizes individual acquisition lines with additional information, such as an ECG trace 504 or a Respiration motion trace. By synchronizing the lines with the ECG trace 504 (e.g., relative to the R wave position), a heart cycle can be reconstructed. Because the heart cycle or respiration motion is periodic, the image can be reconstructed by inserting each acquisition line into its appropriate position relative to, for example, the R wave of the ECG trace 504. In addition, by using a respiration-motion trace, either extracted from an ECG signal or acquired by other means, lines acquired during respiration motion can be identified and optionally excluded from processing, thus limiting motion-induced effects.

Figure 6:
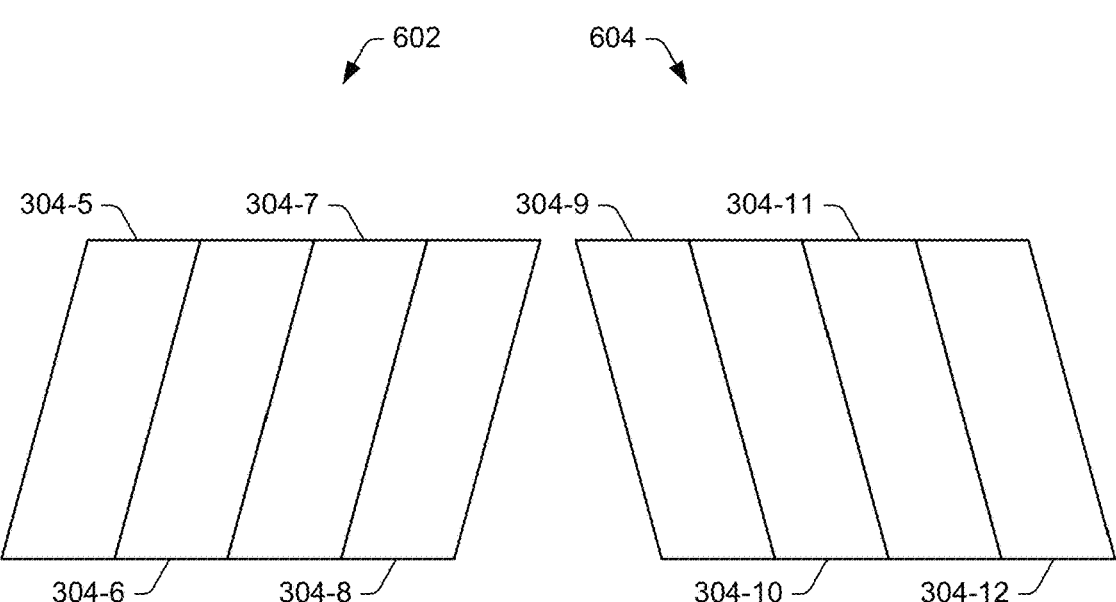
FIG. 6 illustrates an example ultrasound data acquisition at different angles.

FIG. 6 illustrates an example 600 of ultrasound data acquisition at different angles. The anatomy can be observed from different angles (perspectives) by adjusting an angle of transmit and receive beams. In an example, the portions 304 shown in FIG. 3 (acquired in vertical lines) can be acquired at different angles (non-parallel to an axial direction of the ultrasound scanner). As shown in FIG. 6, the full frame can be acquired by shifting the transmit and receive beams to be, for example, 15-20 degrees left (e.g., frame 602) and right (e.g., frame 604). In this way the portions 304 are acquired in frame 602 as portions 304-5, 304-6, 304-7, and 304-8 and in frame 604 as portions 304-9, 304-10, 304-11, and 304-12. Shifting the beamforming angles in this way provides different perspectives of the same anatomy, which can provide additional information to help alleviate edge artifacts between portions because edges appear to be in different locations. Further, by visualizing the data at different angles and combining the data (e.g., beam steering, image compounding, etc.), various artifacts such as speckle and noise artifacts can be reduced, thereby enhancing the image quality. In addition, Doppler signals can be enhanced by adjusting the imaging angle to align closer to a direction which is in-line with the motion. Thus, by shifting the angles doppler signal sensitivity can often be improved.

Using the data acquisition techniques disclosed herein provides other downstream advantages as well. For example, a full FPGA beamformer with focused transmit and receive signals can be used, in contrast to the plane-wave acquisition used in conventional ultrasound systems. Also, the data can be transferred to a host computer in real time and can be streamed to memory in a continuous manner, thus allowing "quasi-unlimited" acquisition times (to a capacity limit of the computer memory (e.g., hard drive)). The amount of data is large but manageable with systems currently available.

Some systems can use periodic scout images, which are images of the entire field of view (FOV) acquired regularly and which serve as displayable real-time updates on the condition of the subject. Such scout images are not necessary to enable the techniques disclosed herein but can be included periodically by inserting them into a frame sequence (ping sequence) of the acquisition. The scout images can be acquired, for example, between acquisition of the blocks, which is convenient as it is done during a natural separation in the data continuity.

Microvasculature imaging is different from conventional electrocardiogram-gated kilohertz visualization (EKV) ultrasound. For example, EKV currently has two types: B-mode EKV and Color EKV. B-mode EKV acquires 8-bit compressed (log compressed, envelope detected) data and constructs a sequence of images synchronized to the ECG cycle, thus enabling the production of a high frame rate cine-loop of the entire heart cycle. Color EKV acquires uncompressed quadrature demodulated (IQ) data. Color EKV also produces a cine-loop of the entire heart cycle; however, additional processing is performed to filter out the stationary signal(s) (clutter filtering) as typical of color flow or power doppler imaging. This processing is performed using a line-based representation of the data. Filtering is performed per sample in a way that is similar to traditional doppler processing. The difference is that instead of performing doppler filtering on 8, 16, or 32 samples (ensemble size), there are seconds of data at the PRF (line-time). Thus, the filter can be quite different and the effective ensemble size can be relatively large, enabling significant increases in doppler sensitivity. For example, other filters can be utilized such as long time Finite Impulse Response (FIR) filters, Infinite Impulse Response (IIR) filters, Singular Value Decomposition (SVD), or Fast Fourier Transform (FFT) or Discrete Fourier Transform (DFT) filters) In the end, the data is still synchronized to the ECG cycle.

In contrast to EKV ultrasound, microvasculature imaging assumes that the anatomy is not heavily affected by the cardiac cycle or that any effect as a measurable quantity is negligible. Microvasculature imaging is directed to providing a single, high-resolution image of small vessels. Thus, microvasculature imaging differs from EKV ultrasound in (i) the acquisition configuration (e.g., line-time, PRF, number of views, the use of compounding, etc.), (ii) the manner of processing, and (iii) the organization of a user interface (UI) for this specific task (e.g., the acquisition dialogs, processing dialogs, etc.). As mentioned, there are several application domains for the processing, two of which are described herein in detail: super-resolution imaging ("bubble tracking") and microvasculature doppler.

Super-Resolution Imaging

Figure 7:
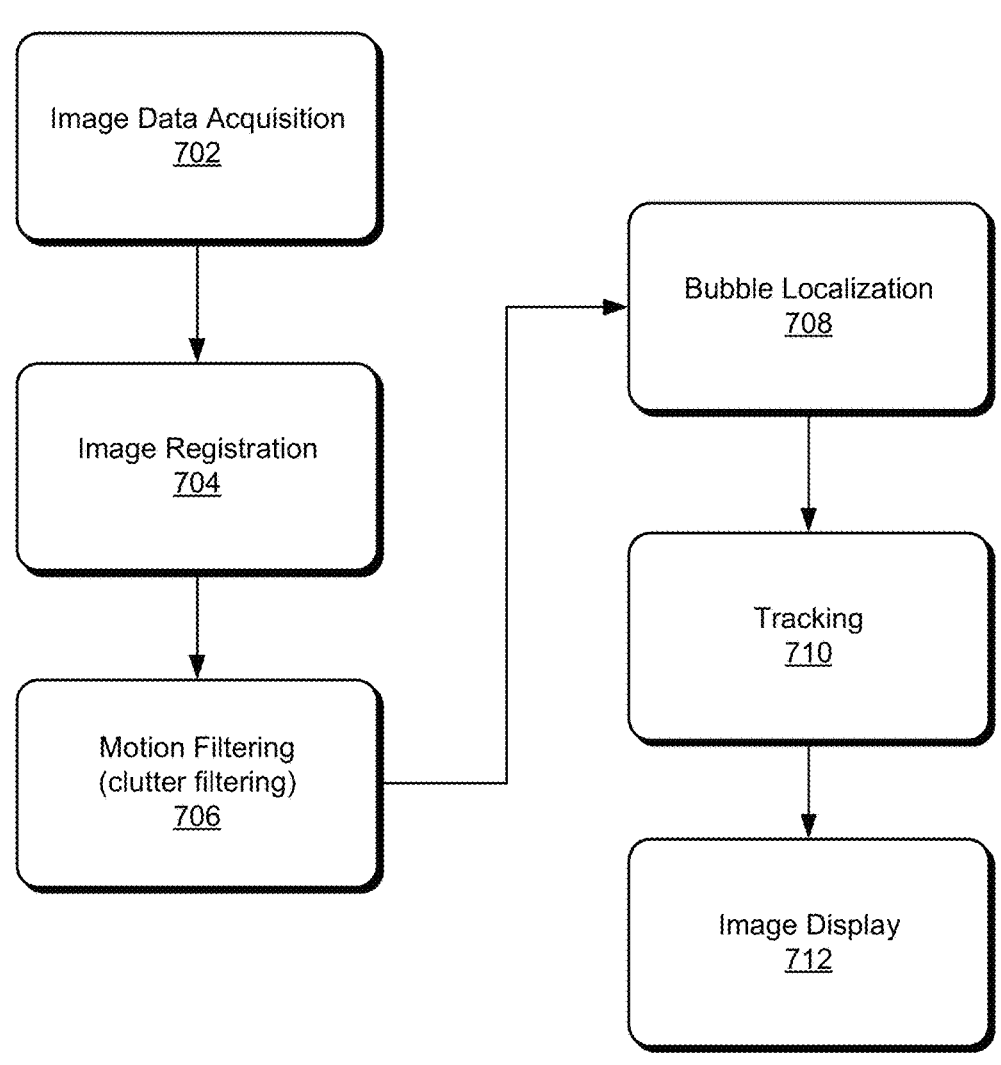
FIG. 7 illustrates an example workflow for super-resolution imaging of ultrasound data.

FIG. 7 illustrates an example workflow 700 for super-resolution imaging of ultrasound data. The first step is image data acquisition 702. For super-resolution imaging, image data is acquired at frame rates exceeding 1,000 fps. This can be achieved by using the data acquisition techniques disclosed herein; in particular, by acquiring small portions of an image at a desired frame rate (e.g., 1,000 fps, 2000 fps, etc.), each portion is acquired repeatedly over a respective duration of time. Then, subsequent processing steps include image registration 704, motion filtering (clutter filtering) 706, bubble localization 708, tracking 710, and image display 712.

The image registration 704 includes establishing a correspondence between images (e.g., the portions 304), such as by transforming different portions 304 into a single coordinate system. The motion filtering 706 removes stationary objects so only moving elements remain (e.g., microbubbles remain and stationary tissue surrounding the microbubbles is removed). The bubble localization 708 locates the microbubbles. For example, the bubble localization 708 includes identifying edges and calculating the centroid and a shape of each microbubble. The centroid and edges can be used to approximate the shape of each microbubble. The tracking 710 tracks the microbubbles as they move across one or more portions 304 of the image over the total acquisition time. For example, the microbubbles are tracked across one portion (e.g., portion 304-1) and separately tracked across another portion (e.g., portion 304-2). The microbubbles can also be tracked as they move between portions 304 (e.g., beyond the edge of one portion and into an adjacent portion). The image display 712 provides a high-resolution display of the tracked microbubbles that move through the vasculature of the anatomy but with stationary tissue filtered out.

Figure 8:
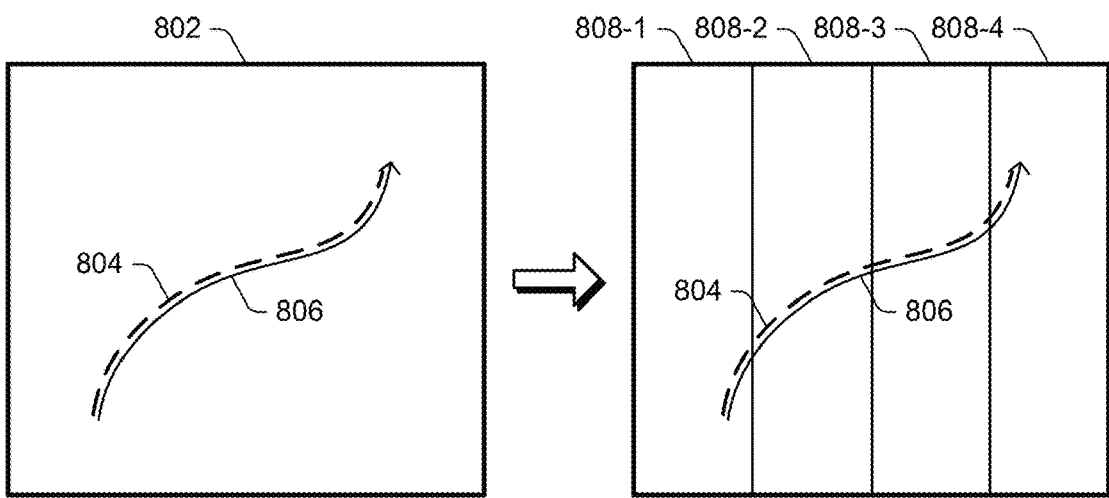
FIG. 8 illustrates an example implementation of a bubble track.

FIG. 8 illustrates an example implementation 800 of a bubble track. Image 802 is a full-frame depiction of an example bubble track 804 moving across an image. The dashed line represents a collection of small "tracklets" (e.g., fragments of a track followed by a moving object, as constructed by an image recognition system) displayed together to visually form a "complete" track (e.g., track 806). These tracklets are short; thus, acquiring smaller sections of the image is not unreasonable. For example, the image can be divided into four or eight sections (e.g., portions 304), such as sections 808-1, 808-2, 808-3, and 808-4. Because the moving objects move slowly and not far throughout the duration of time of the data acquisition, they can be tracked in each section 808.

The width of the sections 808 can depend on a desired final frame rate. To achieve a higher frame rate, smaller portion sizes (e.g., widths) are used, which also results in a greater number of portions and a longer total acquisition time. Depending on the portion width, the number of portions can be, for example, four portions at 1,000 Hz, 8 portions at 2000 Hz, 16 portions at 4000 Hz, etc.

Figure 9:
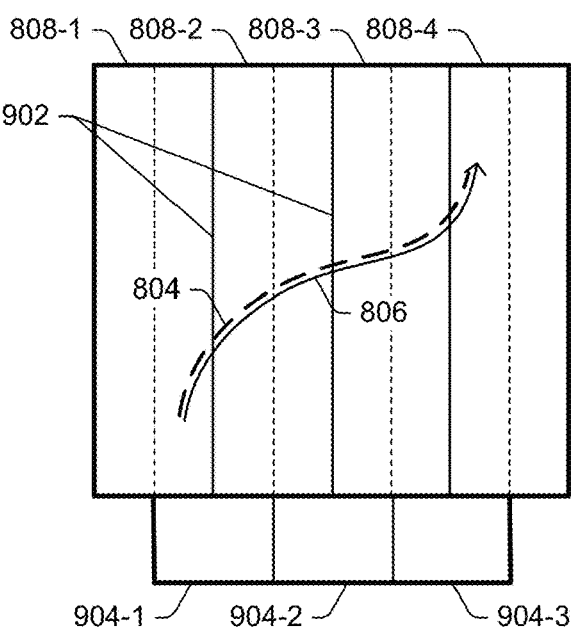
FIG. 9 illustrates an example data acquisition of overlapping portions.

In some cases, the microbubbles move outside a boundary of a section 808 of the image, which can cause discontinuity. Consider FIG. 9, which illustrates an example data acquisition of overlapping portions. To reduce or remove edge artifacts associated with the boundaries (e.g., boundaries 902) between sections 808, additional portions 904 (e.g., portions 904-1, 904-2, and 904-3) can be acquired and offset or shifted to overlap the boundaries 902 between the sections 808. Note the portions 904 are illustrated as vertically offset only for the sake of the reader's understanding (e.g., the additional portions 904 match the vertical component frame of the image and are offset horizontally from the sections 808). These additional portions 904 can be integrated with the sections 808 (e.g., the portions 304) to track the microbubbles moving across the image and provide an image having a continuous track of microbubbles. In some implementations, one or more of the sections 808 can overlap an adjacent section 808 (e.g., section 808-2 can overlap section 808-1 and/or section 808-3), which can reduce edge artifacts at the boundaries of the sections 808 without using the additional portions 904 (e.g., portion 904-1 and/or portion 904-2). In addition, or in the alternative, the additional portions 904 and/or the sections 808 can be integrated with the data from the angled acquisitions (e.g., steered beams) described with respect to FIG. 7 (e.g., the portions 304-5 through 304-12) to provide the continuous track of microbubbles in the displayed image. Using the angled acquisitions as overlapping portions with the sections 808 can provide a different and improved view of blood flow, for example. Color doppler acquisition, for instance, can be steered to improve sensitivity for vessels in which flow moves perpendicular to the transmit beam (flow moving perpendicular to the transmit beam results in no doppler effect).

One of the challenges of using smaller widths for the sections 808 is that smaller portions can make image registration more difficult. For example, registration of gross image motion is most easily done using the entire image. The overlapping portions can help reduce or remove registration artifacts at the edges of each portion. For example, if two large images (full FOV images) are acquired and image registration is performed (e.g., using dense optical flow), errors are encountered around the edges because flow cannot be processed outside the image boundaries. Thus, typically a border region is applied to address the errors at the edges. If the sections 808 are too small, then registration might not be possible. The imaging application generally requires that a subject and transducer be fixed to remove as much motion as possible during acquisition. Registration is an optional step.

The acquisition techniques disclosed herein enable acquisition at high-temporal resolution using an existing hardware beamformer to obtain images without artifacts (both transmit and receive beamforming). Also, with access to physiological signals of the subject, respiration gating during processing is more easily performed compared to conventional plane-wave or B-mode acquisition techniques. The acquisition techniques disclosed herein also enable alternative processing such as doppler processing to obtain other types of data that are less sensitive to challenges and difficulties of bubble tracking. Further, the techniques disclosed herein are not limited to the 8 GB (or 16 GB, for example) FPGA memory limit that limits plane-wave acquisition. Rather, the memory limit of the techniques herein is associated with the storage capacity of the computing device associated with the ultrasound machine. In some implementations, such as an ultrasound system coupled to a cloud computing system, online storage capacity can be essentially unlimited.

The ultrasound system can achieve such long acquisition times in a variety of ways. In one example, each section 808 can be individually acquired for a desired amount of time (e.g., line-time equals 60 seconds). In another example, the ultrasound system can acquire a first portion (e.g., section 808-1) for a relatively short period of time (e.g., 1 to 5 seconds), move to a next portion (e.g., section 808-2) and acquire it for a relatively short period of time (e.g., 1 to 5 seconds), and continue such acquisition pattern from portion to portion until sequentially completing the entire image. Then, the process can be repeated (e.g., repeat acquisition of the first portion, then the next portion, and so on) until the total acquisition time (e.g., 60 seconds) is obtained.

Microvascular Doppler Imaging

As mentioned, microvascular doppler imaging is a high-sensitivity power-doppler technique. However, microvascular doppler imaging is different from traditional doppler processing (e.g., color EKV) in several ways, including filtering. The most important step in conventional color EKV is clutter filtering on its line data. In a line data representation, for example, where one line is 512 samples, there is a line at each PRF interval for a period of 1 to 5 seconds (e.g., 1 second at 1,000 Hz is 1,000 lines). For microvascular doppler imaging, vast amounts of data are not necessary. Perhaps as little as 1 second per line can be acquired. Frequently, however, the subject (e.g., human, animal) is breathing during data acquisition, resulting in respiration motion (which is typically on the order of 1 second per breath).

The acquired data can be filtered in a variety of ways (e.g., using FIR, FFT, DFT, IIR, Singular-Value Decomposition (SVD), etc.) While EKV imaging tends to favor fast-moving blood, microvascular imaging is directed at slow-moving blood, which can be similar to a clutter signal. Filtering can also be performed on the sections 808 in their image form. For example, returning to FIG. 4, the portions 304 can each be treated as a collection of images (e.g., 64×512 pixel images). Image registration can be performed on each image or each collection of pixel images using dense optical flow, for example, or another method such as affine transforms, with horizontal plus vertical shifting to reduce image-toimage motion. Both line-based filtering and image-based filtering constitute the clutter filtering operation. The result is a data set that is primarily only moving blood. Although these methods can be used without microbubbles, microbubble injection can improve the doppler sensitivity of the blood.

At this point, the color EKV processing could start collecting lines synchronized to the ECG cycle. However, because ECG synchronization is optional for microvascular imaging, collection is different from the EKV processing. Although there is no ECG dependence, there is still respiration motion, and simple averaging techniques generally do not filter out motion.

In one example, a respiration signal can be used to identify regions of data that are potentially preferable. The subject might breathe once per second. The ultrasound system can identify this breath motion and select a region where the animal has exhaled. Such a region can be a "motionless" region. Data outside this motionless region can be less reliable and likely unusable; thus, it can be ignored. Ignoring data outside the motionless region reduces the amount of data available for averaging and improves contrast and sharpness of the result. In some implementations, the ultrasound system can include a setting (e.g., configuration parameter) that is selectable (automatically or via user input) to set how much of the respiration period is considered motionless.

In another example, data comparisons are used. Each data line can be compared with each other data line to generate a profile that describes the level of similarity between the data. For example, a sum of absolute differences of two data lines produces a value of zero (0) if the two data lines are identical. The value progressively increases with increasing dissimilarity between the two lines. The ultrasound system can select (based on a setting or user input) to keep only data that exceeds a similarity threshold (e.g., 0.7, 0.75, 0.8, etc.). Alternatively, the ultrasound system can select (based on a setting or user input) to keep only a certain amount of the data (e.g., the most similar 50%, 35%, 25%, etc.).

In yet another example, the data comparisons are performed during the averaging itself, instead of blindly taking two lines and summing them sample-by-sample. The ultrasound system can compare sub-regions of the lines and offset the sample such that the sample better aligns with the source data before summation. For example, if two data lines, which are to be averaged, are slightly offset from each other or are only in some regions, a comparison and shift of each sample can reduce the offset and produce a sharper result than the conventional clutter filtering of color EKV. Using the techniques disclosed herein for microvascular doppler imaging provides a doppler image having sensitivity that significantly exceeds that which can be obtained using existing doppler techniques.

Although both microvasculature doppler imaging and super-resolution imaging produce similar results, there exist some major differences. For example, while super-resolution can theoretically produce a much more detailed, higher-resolution image with a significant number of quantifiable metrics, the acquisition time is long (e.g., minutes). Long acquisition times prevent the use of 3D acquisition techniques. The microvasculature doppler imaging, however, is relatively fast and can complete an image in as little as 3 to 5 seconds. Thus, acquisition of a complete 3D sequence is reasonable (on the order of 30 to 60 seconds depending on the number of frames). In contrast to super-resolution imaging, microvasculature doppler imaging has fewer quantifiable metrics. Also, with respect to time-to-result, super-resolution imaging currently requires over 15 minutes of processing after acquisition but microvasculature doppler imaging can produce an image in approximately 5 seconds or less after acquisition.

Example Methods

Figure 11:
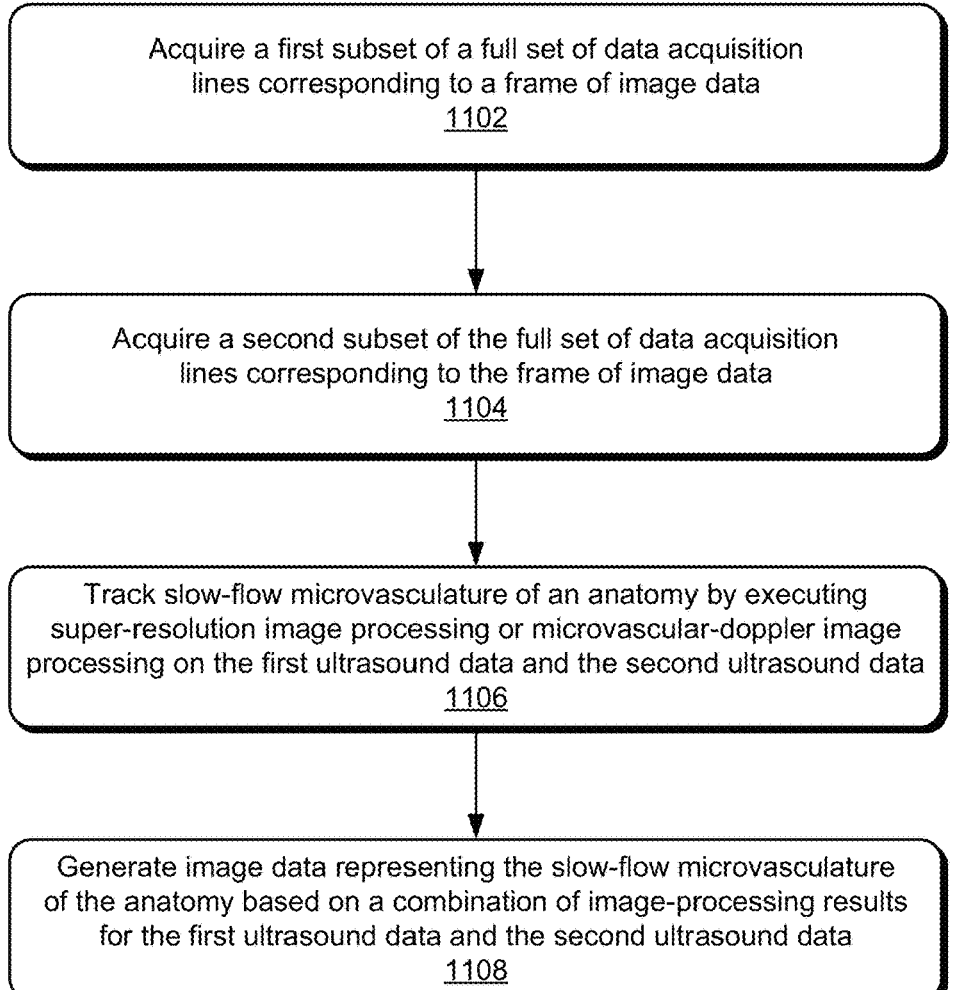
FIG. 11 depicts another method for microvasculature imaging acquisition.

FIGS. 10 and 11 depict methods 1000 and 1100 for microvasculature imaging acquisition. The methods 1000 and 1100 are shown as a set of blocks that specify operations performed but are not necessarily limited to the order or combinations shown for performing the operations by the respective blocks. Further, any of one or more of the operations can be repeated, combined, reorganized, or linked to provide a wide array of additional and/or alternate methods. In portions of the following discussion, reference can be made to the example system 100 of FIG. 1 or to entities or processes as detailed in FIGS. 2-6, reference to which is made for example only. The techniques are not limited to performance by one entity or multiple entities operating on one device.

In FIG. 10, at 1002, first ultrasound data is generated based on reflections of first ultrasound signals transmitted by an ultrasound scanner of an ultrasound system at an anatomy of a subject. For example, the ultrasound scanner 104 of the ultrasound machine 102 can transmit ultrasound signals at the anatomy of the subject (e.g., patient 114), receive reflections of those signals, and generate ultrasound data from the reflections. In implementations, the ultrasound scanner 104 uses a predefined or fixed pulse repetition frequency (PRF) for emitting the ultrasound signals (e.g., pulses). Also, the ultrasound scanner 104 has a maximum frame rate for producing multiple frames of image data from the first ultrasound data over a sector corresponding to a full field of view of the ultrasound scanner 104. The sector has a width corresponding to an image width of the multiple frames. For example, frame 302 in FIG. 3 represents an image frame corresponding to the sector or the full FOV of the ultrasound scanner 104. In aspects, the maximum frame rate is based on the predefined PRF and a number of acquisition lines corresponding to each frame of the image data.

At 1004, a temporal resolution of the ultrasound system is increased responsive to an input. The input can be based on a user input or a setting. The temporal resolution is increased by at least performing operations 1006 and 1008. At 1006, the sector is divided into a plurality of portions that each have fewer acquisition lines than the sector. For example, the frame 302 in FIG. 3 is divided into four portions 304. At 1008, second ultrasound data is generated based on reflections of second ultrasound signals transmitted by the ultrasound scanner within a respective portion of the plurality of portions for a duration of time and at the predefined pulse repetition frequency to achieve a greater frame rate for the respective portion than the maximum frame rate for the sector. For example, individual portions 304 are each scanned repeatedly for a duration of time to produce a sequence of data for each portion, as illustrated in FIG. 4. By scanning only a small portion of the sector at the same PRF as the entire sector, the frame rate usable for the portion becomes greater than the frame rate usable for the entire sector.

In some implementations, the second ultrasound data is generated using standard imaging protocols that provide one acquisition line per transmit pulse. In other implementations, the second ultrasound data is generated using imaging protocols that provide two or more acquisition lines per transmit pulse. The greater frame rate can be equal to or greater than 1,000 frames per second. Also, at least some of the second ultrasound signals transmitted by the ultrasound scanner include one or more steered transmit beams for generating at least some of the second ultrasound data at one or more different directions that are non-parallel to an axial direction of the ultrasound scanner. In some implementations, at least some of the portions are aligned relative to an axial direction of the ultrasound scanner.

In implementations, the ultrasound data is acquired for each portion individually and separately from other portions of the plurality of portions. Additionally, the method 1000 can include transmitting the second ultrasound signals at the anatomy repeatedly for the duration of time over the respective portion of the plurality of portions and at the predefined pulse repetition frequency and receiving the reflections of the second ultrasound signals. Further, generating the second ultrasound data can include generating ultrasound data for a first portion of the sector over first time period and after expiration of the first time period, generating ultrasound data for a second portion of the sector for a second time period.

Optionally, the second ultrasound data can be synchronized with physiological signals of the subject. For example, the ultrasound data can be synchronized with information from an ECG cycle to reconstruct a heart cycle. In another example, the ultrasound data can be synchronized with a respiration motion trace to filter out motion such as when the subject is actively breathing in or out.

At 1010, super-resolution image processing or microvascular-doppler image processing is executed on the second ultrasound data for each portion to track slow-flow microvasculature of the anatomy in each portion. In some aspects, the super-resolution image processing or the microvascular-doppler image processing includes filtering out reflected ultrasound signals representing stationary tissue of the anatomy.

At 1012, results of the super-resolution image processing or microvascular-doppler image processing for each portion are compounded to provide compounded results for the sector. For example, the results of the image processing are compounded to generate image data for the entire sector and, thus, an entire frame. Compounding the results can also help to remove edge artifacts associated with the boundaries of each portion.

At 1014, based on the compounded results, the image data is generated for rendering an image representing the slow-flow microvasculature of the anatomy over the sector. At this point, the image data is generated for an entire frame based on ultrasound data acquired at a much greater frame rate than was possible by conventional techniques that scan the entire sector all at once.

In FIG. 11, at 1102, a first subset of a full set of data acquisition lines associated with an ultrasound image is acquired, by an ultrasound system, repeatedly over a first time period and at a first frame rate to generate first ultrasound data. The ultrasound data represents reflections of ultrasound signals transmitted by an ultrasound scanner of the ultrasound system at an anatomy of a subject. The first subset has fewer data acquisition lines than the full set. Also, the first frame rate is greater than a maximum frame rate usable by the ultrasound system to acquire the full set of data acquisition lines of the ultrasound image.

In some implementations, the first subset is acquired using steered transmit beams to acquire at least some of the first subset at one or more directions that are non-parallel to an axial direction of the ultrasound scanner. In one example, the first subset of data acquisition lines is acquired using standard imaging protocols that provide one acquisition line per transmit pulse. In another example, the first subset of data acquisition lines is acquired using imaging protocols that provide two acquisition lines per transmit pulse. In implementations, some of the first subset is acquired using transmit beams that are aligned to the axial direction of the ultrasound scanner.

At 1104, a second subset of the full set of data acquisition lines associated with the ultrasound image is acquired, by the ultrasound system and independent of the first subset of the data acquisition lines, repeatedly over a second time period and at a second frame rate to generate second ultrasound data. The second frame rate is greater than the maximum frame rate usable to acquire the full set of the data acquisition lines. Also, the second subset has fewer data acquisition lines than the full set. In aspects, the acquisition of the second subset is initiated after expiration of the first time period. In some implementations, the second subset is acquired using steered transmit beams to acquire at least some of the second subset at one or more directions that are non-parallel to the axial direction of the ultrasound scanner. In implementations, some of the second subset is acquired using transmit beams that are aligned to the axial direction of the ultrasound scanner. Also, the second subset is acquired individually and separately from the first subset.

In some implementations, the first frame rate and the second frame rate are each equal to or greater than 1,000 fps. In one example, the second subset of data acquisition lines is acquired using standard imaging protocols that provide one acquisition line per transmit pulse. In another example, the second subset of data acquisition lines is acquired using imaging protocols that provide two or more acquisition lines per transmit pulse.

At 1106, the first ultrasound data and the second ultrasound data are processed to track slow-flow microvasculature of the anatomy. In aspects, the first ultrasound data and the second ultrasound data are processed using super-resolution imaging processing or microvascular-doppler image processing. In some implementations, the first ultrasound data and the second ultrasound data are synchronized with physiological signals of the subject. In some examples, the first ultrasound data and the second ultrasound data are processed separately from one another.

At 1108, an image representing the slow-flow microvasculature of the anatomy is generated based on the first ultrasound data and the second ultrasound data. In some implementations, the ultrasound data of each portion is compounded to generate the image of the slow-flow microvasculature over the full set of data acquisition lines.

CONCLUSION

Embodiments of microvasculature imaging acquisition are disclosed are advantageous, as they enable generation of high-resolution, high-sensitivity images for low-intensity, slow-flow vasculature of anatomy. The imaging acquisition techniques disclosed herein provide solutions that enable super-resolution imaging and microvascular-doppler imaging of microvasculature.

What is claimed is:

1. A method comprising:
  generating first ultrasound data based on reflections of first ultrasound signals transmitted by an ultrasound scanner of an ultrasound system at an anatomy of a subject, the ultrasound scanner having a predefined pulse repetition frequency (PRF) for emitting the first ultrasound signals, the ultrasound scanner having a maximum frame rate for producing multiple frames of image data from the first ultrasound data over a sector corresponding to a full field of view (FOV) of the ultrasound scanner, the sector having a width corresponding to an image width of the multiple frames, the maximum frame rate being based on the predefined PRF and a number of acquisition lines corresponding to each frame of the image data;

responsive to an input, increasing a temporal resolution of the ultrasound system by:

dividing the sector into a plurality of portions that each have fewer acquisition lines than the sector;

causing the ultrasound scanner to transmit second ultrasound signals within a respective portion of the plurality of portions repeatedly for a duration of a line-time and at the predefined PRF to achieve a greater frame rate for the respective portion than the maximum frame rate for the sector, wherein the second ultrasound signals are transmitted repeatedly within a first portion of the plurality of portions for the duration of the line-time prior to being transmitted repeatedly within a second portion of the plurality of portions for the duration of the line-time;

generating second ultrasound data based on reflections of the second ultrasound signals; and between acquisition of two respective portions of the plurality of portions, acquiring a scout image of the full FOV of the ultrasound scanner and inserting the scout image into a frame sequence of the acquisition of the two respective portions;

tracking slow-flow microvasculature of the anatomy in each portion by executing super-resolution image processing or microvascular-doppler image processing on the second ultrasound data for each portion;

compounding results of the super-resolution image processing or the microvascular-doppler image processing for each portion to provide compounded results for the sector; and generating, based on the compounded results, the image data for rendering an image representing the slow-flow microvasculature of the anatomy over the sector.

2. The method of claim 1, wherein the second ultrasound data is generated using standard imaging protocols that provide one acquisition line per transmit pulse.

3. The method of claim 1, wherein the second ultrasound data is generated using imaging protocols that provide two acquisition lines per transmit pulse.

4. The method of claim 1, wherein at least some of the second ultrasound signals transmitted by the ultrasound scanner include one or more steered transmit beams for generating at least some of the second ultrasound data at one or more different directions that are non-parallel to an axial direction of the ultrasound scanner.

5. The method of claim 1, wherein at least some of the portions are aligned relative to an axial direction of the ultrasound scanner.

6. The method of claim 1, further comprising synchronizing the second ultrasound data with physiological signals of the subject.

7. The method of claim 1, further comprising:

transmitting the second ultrasound signals at the anatomy repeatedly for the duration of the line-time over the respective portion of the plurality of portions and at the predefined PRF; and receiving the reflections of the second ultrasound signals.

8. The method of claim 1, wherein generating the second ultrasound data includes generating the second ultrasound data for each portion of the plurality of portions individually and separately from other portions of the plurality of portions.

9. The method of claim 1, wherein executing the super-resolution image processing or the microvascular-doppler image processing includes filtering out reflected ultrasound signals representing stationary tissue of the anatomy.

10. The method of claim 1, wherein at least two portions of the plurality of portions are non-overlapping.

11. The method of claim 1, wherein at least one portion of the plurality of portions overlaps a boundary of at least one other portion of the plurality of portions.

12. The method of claim 1, further comprising providing displayable real-time updates of the anatomy of the subject based on periodic scout images acquired between the portions of the plurality of portions.

13. An ultrasound system comprising:

an ultrasound scanner having a predefined pulse repetition frequency (PRF) for emitting ultrasound signals and a maximum frame rate for producing multiple frames of image data from detected reflections of the ultrasound signals emitted over a sector corresponding to a full field of view (FOV) of the ultrasound scanner, the sector having a width corresponding to an image width of the multiple frames, the maximum frame rate being based on the predefined PRF and a number of acquisition lines corresponding to each frame of the image data, the ultrasound scanner configured to, in response to an input:

divide the sector into a plurality of portions;

transmit, at an anatomy of a subject, the ultrasound signals within a respective portion of the plurality of portions repeatedly for a duration of a line-time using the predefined PRF to achieve a frame rate for the respective portion that is greater than the maximum frame rate for the sector, the ultrasound signals transmitted repeatedly within a first portion of the plurality of portions for the duration of the line-time prior to being transmitted repeatedly within a second portion of the plurality of portions for the duration of the line-time;

generate ultrasound data for the respective portion of the plurality of portions based on detected reflections of the ultrasound signals transmitted within the respective portion; and between acquisition of two respective portions of the plurality of portions, acquire a scout image of the full FOV of the ultrasound scanner and insert the scout image into a frame sequence of the acquisition of the two respective portions;

one or more computer processors; and one or more computer-readable media having instructions stored thereon that, responsive to execution by the one or more computer processors, implement one or more modules, the one or more modules configured to:

execute super-resolution image processing or microvascular-doppler image processing on the ultrasound data for each portion to provide image-processing results for tracking slow-flow microvasculature of the anatomy; and generate the image data for rendering an image representing the slow-flow microvasculature of the anatomy over the sector based on a combination of the image-processing results of the ultrasound data for each portion.

14. The ultrasound system of claim 13, wherein the ultrasound scanner is configured to steer at least some of the transmitted ultrasound signals in one or more directions that are non-parallel to an axial direction of the ultrasound scanner.

15. The ultrasound system of claim 13, wherein the one or more modules are configured to synchronize the ultrasound data with physiological signals of the subject.

16. The ultrasound system of claim 13, wherein the one or more modules are further configured to compound the image-processing results of the ultrasound data for each portion to generate the image data of the slow-flow micro-vasculature over the sector.

17. The ultrasound system of claim 13, wherein the frame rate is equal to or greater than 1,000 frames per second and the ultrasound data is generated at one line per transmit pulse by the ultrasound scanner.

18. The ultrasound system of claim 13, wherein the plurality of portions includes at least two non-overlapping portions.

19. A method comprising:

acquiring, by an ultrasound system having an ultrasound scanner with a fixed pulse repetition frequency (PRF) for emitting ultrasound signals, a first subset of a full set of data acquisition lines corresponding to a frame of image data, the first subset acquired repeatedly for a first line-time using a first frame rate and the fixed PRF to generate first ultrasound data, the ultrasound data representing reflections of the ultrasound signals transmitted by the ultrasound scanner at an anatomy of a subject, the first subset having fewer data acquisition lines than the full set;

after acquiring the first subset of the full set of data acquisition lines, acquiring a scout image of the full set of data acquisition lines;

after acquiring the scout image, acquiring, by the ultrasound system and independent of the first subset of the data acquisition lines, a second subset of the full set of data acquisition lines corresponding to the frame of image data, the second subset acquired repeatedly for a second line-time period using a second frame rate and the fixed PRF to generate second ultrasound data, the second subset having fewer data acquisition lines than the full set;

inserting the scout image into a frame sequence of the first subset and the second subset;

tracking slow-flow microvasculature of the anatomy by executing super-resolution image processing or micro-vascular-doppler image processing on the first ultra-sound data and the second ultrasound data; and generating image data representing the slow-flow micro-vasculature of the anatomy based on a combination of image-processing results for the first ultrasound data and the processed second ultrasound data.

20. The method of claim 19, wherein the acquiring of the second subset is initiated after expiration of the first line-time.

21. The method of claim 19, wherein:

acquiring the first subset includes using steered transmit beams to acquire at least some of the first subset at one or more directions that are non-parallel to an axial direction of the ultrasound scanner; and acquiring the second subset includes using steered trans-mit beams to acquire at least some of the second subset at one or more directions that are non-parallel to the axial direction of the ultrasound scanner.

\* \* \* \* \*